United States Patent
Gennaro

(10) Patent No.: US 9,216,203 B1
(45) Date of Patent: Dec. 22, 2015

(54) NATURAL HEALTH SUPPLEMENT

(71) Applicant: Franco Gennaro, Doral, FL (US)

(72) Inventor: Franco Gennaro, Doral, FL (US)

(73) Assignee: Franco F. Gennaro, Miami, FL (US)

( * ) Notice: Subject to any disclaimer, the term of this patent is extended or adjusted under 35 U.S.C. 154(b) by 339 days.

(21) Appl. No.: 13/869,105

(22) Filed: Apr. 24, 2013

(51) Int. Cl.
| | | |
|---|---|---|
| *A61K 36/8962* | (2006.01) | |
| *A61K 35/644* | (2015.01) | |
| *A61K 31/23* | (2006.01) | |
| *A61K 36/28* | (2006.01) | |
| *A61K 36/31* | (2006.01) | |
| *A61K 36/54* | (2006.01) | |
| *A61K 36/73* | (2006.01) | |
| *A61K 36/752* | (2006.01) | |
| *A61K 36/81* | (2006.01) | |
| *A61K 36/88* | (2006.01) | |
| *A61K 36/9068* | (2006.01) | |

(52) U.S. Cl.
CPC .............. *A61K 35/644* (2013.01); *A61K 31/23* (2013.01); *A61K 36/28* (2013.01); *A61K 36/31* (2013.01); *A61K 36/54* (2013.01); *A61K 36/73* (2013.01); *A61K 36/752* (2013.01); *A61K 36/81* (2013.01); *A61K 36/88* (2013.01); *A61K 36/8962* (2013.01); *A61K 36/9068* (2013.01)

(58) Field of Classification Search
None
See application file for complete search history.

(56) References Cited

U.S. PATENT DOCUMENTS

| 8,518,435 B2 * | 8/2013 | Barron ........................ 424/439 |
| 2009/0238905 A1 * | 9/2009 | Gurney et al. ................ 424/756 |

* cited by examiner

*Primary Examiner* — Susan Hoffman
(74) *Attorney, Agent, or Firm* — Albert Bordas, P.A.

(57) ABSTRACT

A natural antibiotic health supplement, having garlic, onion, horseradish root, cayenne or habanero peppers, ginger, organic unfiltered apple cider vinegar, unfiltered raw honey, cinnamon, *echinacea*, and monolaurin. The natural antibiotic health supplement is effective to support a person's immune system, and especially when it detects various common strains of viruses, bad bacteria, and infections.

1 Claim, No Drawings

NATURAL HEALTH SUPPLEMENT

BACKGROUND OF THE INVENTION

1. Field of the Invention

The present invention relates to health supplements, and more particularly, to natural antibiotic health supplements to support an immune system.

2. Description of the Related Art

Applicant is not aware of any natural antibiotic health supplements comprising: garlic, white onion, horseradish root, cayenne or habanero peppers, ginger, organic unfiltered apple cider vinegar, raw honey, lemon juice, cinnamon, *Echinacea*, and monolaurin to support an immune system.

SUMMARY OF THE INVENTION

The instant invention is a natural antibiotic health supplement having ingredients prepared in a specific manner. More specifically, the instant invention is a natural antibiotic health supplement, comprising: garlic, onion, horseradish root, cayenne or habanero peppers, ginger, organic unfiltered apple cider vinegar, unfiltered raw honey, cinnamon, *echinacea*, and monolaurin. The natural antibiotic health supplement may further comprise lemon juice.

To prepare the natural antibiotic health supplement, the cayenne or habanero peppers having seeds are divided approximately in half. The seeds are removed and the cayenne or habanero peppers are chopped. The horseradish root is grated. The ginger is grated. The onion is divided and chopped. The garlic is peeled, divided by cloves, and chopped. Then the chopped cayenne or habanero peppers, the grated horseradish root, the grated ginger, the chopped onion, and the garlic are placed into a first container to form a first mixture.

The organic unfiltered apple cider vinegar is poured into the first container to form a second mixture to settle, and the first container is sealed with a lid thereon. The first container is placed in a controlled temperature approximately between 65°-95°. Approximately every 12 hours, or at least approximately every 24 hours, the first container is flipped to permit the second mixture to continue settling for at least 2 weeks to 1 months time to ensure that the second mixture is thoroughly mixed and distributed evenly to form a third mixture.

The third mixture is strained from the first container into a second container with a fine woven strainer, coffee filter, or clean cloth napkin.

The unfiltered raw honey, the cinnamon, the *Echinacea*, and the monolaurin is added into the second container to make a fourth mixture. The fourth mixture can be consumed in daily quantities approximately between ½ tablespoon, 1-2 times daily to 1-2 large tablespoons is 2-3 times daily. The fourth mixture supports an immune system, especially when attacked by strains of viruses, bad bacteria, and infections, and improves overall wellbeing.

It is therefore one of the main objects of the present invention to provide a natural antibiotic health supplement comprising garlic, white onion, horseradish root, cayenne or habanero peppers, ginger, organic unfiltered apple cider vinegar, raw honey, lemon juice, cinnamon, *Echinacea*, and monolaurin.

It is another object of this invention to provide a natural antibiotic health supplement formulated to support a person's immune system.

It is another object of this invention to provide a natural antibiotic health supplement formulated to improves a person's overall wellbeing.

It is yet another object of this invention to provide such a natural antibiotic health supplement that is inexpensive to prepare and maintain while retaining its effectiveness.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The instant invention is a natural antibiotic health supplement. A health supplement, also known as dietary supplement or nutritional supplement, is a preparation intended to supplement a diet and provide nutrients, such as vitamins, minerals, fiber, fatty acids, or amino acids, that may be missing or may not be consumed in sufficient quantities in a person's diet. Some countries define dietary supplements as foods, while in others they are defined as drugs or natural health products. Supplements containing vitamins or dietary minerals are included as a category of food in the Codex Alimentarius, a collection of internationally recognized standards, codes of practice, guidelines and other recommendations relating to foods, food production and food safety.

The immune system is a system of biological structures and processes within an organism that protects against disease. To function properly, an immune system must detect a wide variety of agents, from viruses to parasitic worms, and distinguish them from the organism's own healthy tissue. In particular, a person's immune system on occasion is attacked by strains of viruses, bad bacteria, and infections.

The present invention, a natural antibiotic health supplement, when prepared properly with fresh ingredients, can be very effective to support a person's immune system when it detects various common strains of viruses, bad bacteria, and infections. Applicant's research and case studies conducted clearly demonstrate the effectiveness of the present invention. The present invention is a powerful alternative to the overdependence of harsh pharmaceutical antibiotics that have been shown to kill a person's natural probiotics, and in many cases contribute to antibiotic resistance, making antibiotics less effective when truly needed for life threatening illnesses.

The natural antibiotic health supplement, object of the present invention, comprises:

garlic: *Allium sativum*, commonly known as garlic, is a species in the onion genus, *Allium*. Its close relatives include the onion, shallot, leek, chive, and rakkyo;

white onion: *Allium cepa*, also known as the bulb onion or common onion, is used as a vegetable and is the most widely cultivated species of the genus *Allium*;

horse radish root: *Armoracia rusticana, Cochlearia armoracia*, is a perennial plant of the Brassicaceae family (which also includes mustard, wasabi, broccoli, and cabbage) and is cultivated primarily for its large, white, tapered root;

cayenne peppers: a cultivar of *Capsicum annuum* related to bell peppers, jalapeños, and others. The *Capsicum* genus is in the nightshade family, Solanaceae. Also known as the Guinea spice, cow-horn pepper, aleva, bird pepper, or, especially in its powdered form, red pepper is a hot chili pepper; or habanero peppers: *Capsicum chinense*, a variety of cayenne peppers; ginger: the rhizome of the plant *Zingiber* official, genus and family Zingiberaceae;

organic unfiltered apple cider vinegar;
unfiltered raw honey;
lemon juice (optional);
cinnamon;

*echinacea*: is a genus, or group of herbaceous flowering plants in the daisy family, Asteraceae; and monolaurin: glycerol monolaurate, glyceryl laurate or 1-Lauroyl-rac-glycerol, is a monoglyceride. It is the mono-esterformed from glycerol and lauric acid. Its chemical formula is $C_{15}H_{30}O_4$.

As an example, the following quantities/amounts make approximately 32 ounces of the natural antibiotic health supplement, object of the present invention:

1 bulb of garlic;
1 large white onion;
1 horse radish root (grated will make approximately 1½ cups);
1 cupful of cayenne or habanero peppers;
1 clump of ginger (grated will make approximately 1½ cups);
16 ounces of organic unfiltered apple cider vinegar;
1 teaspoon of unfiltered raw honey;
lemon juice (optional);
½ teaspoon of cinnamon;
½ teaspoon of *echinacea*; and
½ teaspoon of monolaurin.

In a preferred embodiment, the natural antibiotic health supplement, object of the present invention is prepared as follows:

Secure a first container comprising a tight-fitting lid. In a preferred embodiment, the first container is 32 oz. or larger;

Divide in half the 1 cupful of cayenne or habanero peppers. Remove seeds, and chop the 1 cupful of cayenne or habanero peppers in small pieces;

Grate the 1 horseradish root to make approximately 1½ cups. Grating should be medium to fine;

Grate the 1 clump of ginger to make approximately 1½ cups);

Divide and chop the 1 large white onion in small chunks;
Peel, divide by cloves, and finely chop the 1 bulb of garlic;
Add all of the ingredients listed above into the first container to form a first mixture;

Pour the 16 ounces of organic unfiltered apple cider vinegar into the first container to form a second mixture. Let the second mixture settle, and secure the tight-fitting lid thereon;

Place the first container with the second mixture and having the tight-fitting lid thereon in a controlled temperature. In a preferred embodiment, the controlled temperature is approximately 65°-95°;

Approximately every 12 hours, or at least approximately every 24 hours, flip the first container to permit the second mixture within to continue settling. As an example, assuming the first container initially is right-side up, simply place it upside-down. Then after approximately the twelfth hour, or at least approximately every 24 hours, flip it right-side up again, and continue for approximately 2 weeks to 1 months time. The flipping ensures that the second mixture is thoroughly mixed and distributed evenly to form a third mixture;

Strain the third mixture from the first container into a second container. In a preferred embodiment, the second container is 10-16 oz. In a preferred embodiment, straining is performed with a fine woven strainer, coffee filter, or clean cloth napkin;

Add 1 teaspoon of unfiltered raw honey; lemon juice (optional for taste preference); ½ teaspoon of cinnamon; ½ teaspoon of *echinacea*; and ½ teaspoon of monolaurin into the second container to make a fourth mixture.

Greater or lesser amounts of the natural antibiotic health supplement may of course be made while keeping the proportionalities approximately the same as defined above.

As a natural antibiotic health supplement, the present invention is formulated to support a person's immune system, especially when attacked by strains of viruses, bad bacteria, and infections, and to improve a person's overall wellbeing. The effectiveness of the natural antibiotic health supplement is dependent on how soon it is used when symptoms of strains of viruses, bad bacteria, and infections are realized, and also the severity of the symptoms. Most individuals begin to experience a clearing of the strains of viruses, bad bacteria, and infections symptoms in approximately 24-48 hours. Rest, nutrition, and proper hydration also help.

The natural antibiotic health supplement can be consumed in quantities of approximately 1-2 large tablespoons (1-1.5 oz. preferably on empty stomach) when symptoms of strains of viruses, bad bacteria, and infections are first realized. Such strains of viruses, bad bacteria, and infections include, but are not limited to sore throat, cough, phloem, congestion, or other cold/flu symptoms.

In a preferred method of administration, gargling for a few seconds is beneficial before swallowing. And, abstaining from additional foods and liquids within 1 hour of administration is preferred for optimal effect. A daily dose of the 1-2 large tablespoons is 2-3 times daily until symptoms improve.

The natural antibiotic health supplement does not require refrigeration, and is safe during pregnancy. It can be also administered to children in smaller doses approximately ½ tablespoon, 1-2 times daily.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A natural antibiotic health supplement, consisting of:
A) garlic;
B) onion;
C) horseradish root;
D) cayenne or habanero peppers;
E) ginger;
F) organic unfiltered apple cider vinegar;
G) unfiltered raw honey;
H) cinnamon;
I) *echinacea*;
J) monolaurin; and
K) lemon juice;
said cayenne or habanero peppers having seeds are divided approximately in half, said seeds are removed and said cayenne or habanero peppers are chopped, said horseradish root is grated, said ginger is grated, said onion is divided and chopped, said garlic is peeled, divided by cloves, and chopped;
said chopped cayenne or habanero peppers, said grated horseradish root, said grated ginger, said chopped onion, and said garlic are placed into a first container to form a first mixture;
said organic unfiltered apple cider vinegar is poured into said first container to form a second mixture to settle, and said first container is sealed with a lid thereon;
said first container is placed in a controlled temperature approximately between 65°-95°;
between every 12 to 24 hours, said first container is flipped to permit said second mixture to continue settling for a period of time between 2 weeks to 1 month to ensure that said second mixture is thoroughly mixed and distributed evenly to form a third mixture;

said third mixture is strained from said first container into a second container with a fine woven strainer, coffee filter, or clean cloth napkin;

said unfiltered raw honey, said cinnamon, said *Echinacea*, and said monolaurin is added into said second container to make a fourth mixture;

said fourth mixture is consumed in daily quantities approximately between ½ tablespoon, 1-2 times daily to 1-2 tablespoons, 2-3 times daily; and said fourth mixture supports an immune system when affected by strains of viruses, bacteria, and infections.

\* \* \* \* \*